United States Patent
Castrogiovanni (10) Patent No.: US 10,959,889 B2
(45) Date of Patent: Mar. 30, 2021

(54) DIPOSABLE ABSORBENT PANTS WITH CONTAINMENT SYSTEM

(71) Applicant: Nicole Castrogiovanni, Los Angeles, CA (US)

(72) Inventor: Nicole Castrogiovanni, Los Angeles, CA (US)

(*) Notice: Subject to any disclaimer, the term of this patent is extended or adjusted under 35 U.S.C. 154(b) by 0 days.

(21) Appl. No.: 16/533,604

(22) Filed: Aug. 6, 2019

(65) Prior Publication Data

US 2019/0358095 A1 Nov. 28, 2019

Related U.S. Application Data

(63) Continuation of application No. 15/050,242, filed on Feb. 22, 2016, now Pat. No. 10,413,455.

(51) Int. Cl.

| A61F 13/00 | (2006.01) |
| A61F 13/511 | (2006.01) |
| A61F 13/496 | (2006.01) |
| A61F 13/514 | (2006.01) |
| A61F 13/534 | (2006.01) |
| A61F 13/539 | (2006.01) |
| A61F 13/53 | (2006.01) |

(52) U.S. Cl.
CPC ...... *A61F 13/51104* (2013.01); *A61F 13/496* (2013.01); *A61F 13/51458* (2013.01); *A61F 13/534* (2013.01); *A61F 13/539* (2013.01); *A61F 2013/530007* (2013.01); *A61F 2013/530255* (2013.01); *A61F 2013/530299* (2013.01); *A61F 2013/530343* (2013.01); *A61F 2013/530481* (2013.01)

(58) Field of Classification Search
CPC ............ A61F 13/51108; A61F 13/5146; A61F 5/1476; A61F 13/534; A61F 13/53436; A61F 13/5121; A61F 2013/51361; A61F 2013/530481; A61F 2013/530343; A61F 2013/530299; A61F 2013/530255; A61F 2013/530007; A61F 13/539; A61F 13/51458; A61F 13/496; A61F 13/51104
See application file for complete search history.

(56) References Cited

U.S. PATENT DOCUMENTS

| 4,895,568 | A | * | 1/1990 | Enloe | A61F 13/4758 |
| | | | | | 604/385.27 |
| 6,156,022 | A | * | 12/2000 | Hedlund | A61F 13/495 |
| | | | | | 604/385.29 |
| 6,436,081 | B1 | * | 8/2002 | Wada | A61F 13/4752 |
| | | | | | 604/385.01 |
| 10,413,455 | B2 | * | 9/2019 | Castrogiovanni | |
| | | | | | A61F 13/49413 |
| 2015/0018794 | A1 | * | 1/2015 | Noda | A61F 13/15707 |
| | | | | | 604/372 |
| 2015/0283000 | A1 | * | 10/2015 | Faulks | A61F 13/51104 |
| | | | | | 604/385.101 |

* cited by examiner

*Primary Examiner* — Steven O Douglas
(74) *Attorney, Agent, or Firm* — Sarah M Walkington

(57) ABSTRACT

An absorbent pant is provided with a containment system defined by a wearing-facing surface of the absorbent pant. The containment system comprises at least one of the following: a pleated section comprising a plurality of pleats; a channeled section comprising a plurality of alternating ridges and channels; and/or a bubbled section comprising a plurality of hemispherical-shaped bubbles aligned in a plurality of rows.

11 Claims, 4 Drawing Sheets

DIPOSABLE ABSORBENT PANTS WITH CONTAINMENT SYSTEM

FIELD OF THE INVENTION

The invention relates generally to disposable absorbent pants, such as diapers, training pants, adult incontinence articles, absorbent underwear, and the like, and in particular, disposable absorbent pants with a containment system that reduces the incidence of leakage and/or blowouts, improves handling and containment of liquid and waste during use, and minimizes the amount of moisture in contact with the wearer's skin to enhance air circulation near the wearer's skin.

BACKGROUND OF THE INVENTION

Disposable absorbent pants for receiving and retaining bodily discharges such as urine or feces are well known in the art. Examples of these include disposable diapers, training pants, adult incontinence articles, absorbent underwear, and the like (herein referred to collectively as "diaper(s)" and "absorbent pant(s)"). Traditionally, disposable diapers comprise a liquid permeable inner layer that faces the wearer's body, a liquid impermeable outer layer that faces the wearer's clothing, and an absorbent layer interposed between the inner layer and the outer layer.

Since their introduction into the market place, disposable diapers have continued to improve in terms of comfort, fit, and functionalities, such as absorption capacity. Absorption capacity is quite important for diapers, and many attempts have been made to increase absorption of disposable diapers without undesirably compromising the comfort and fit of the diaper.

Even with these attempts to increase absorption capacity, diaper leaks and blowouts are still common. Leaks can occur, for example, if the disposable diaper is not the correct size for the wearer. A diaper that is too small can be prone to leaking because there isn't enough absorbent material for the volume of liquid. Likewise, a diaper that is too big may also leak because it does not fits snugly around the waist and legs of the wearer, and liquid may leak out at these areas before it can be absorbed. Leaks can also occur when a large volume of liquid is discharged in the diaper at a rate that exceeds the absorption rate of the diaper.

Furthermore, even the most absorbent diapers cannot generally prevent diaper blowouts, where waste escapes from the diaper. Blowouts can occur when the waste has a consistency that is too big to cross the liquid permeable inner layer into the absorbent layer and therefor collects inside the diaper on the inner layer. Blowouts tend to happen at the upper front and/or back edge of the diaper where it is hardest to create a seal between the diaper and the wearer's body.

Existing diapers do not adequately address the problem of diaper leakage and blowouts because the inner layer is generally flat on the inside, with no structure capable of physically capturing and containing excess liquid and/or waste that is not absorbed by the diaper. The excess liquid and/or waste simply gets pushed up and out of the top and sides of the diaper.

Furthermore, because of the generally flat inner layer of existing diapers, the inner layer lays flat against the wearer's skin. There is generally no space between the surface of the inner layer and the wearer's skin to allow air circulation in the area. When the inner layer is wet, this can result in increased odor and irritation of the wearer's skin in the area.

Accordingly, there is a need for improved disposable diapers with structure that can adequately contain excess liquid and/or waste and reduce the incidence of leakage and/or blowouts. There is a need for improved disposable diapers with structure that can provide improved handling of liquid and/or waste and more effectively intake and contain liquid and/or waste during use. Further, there is a need for disposable diapers with structure that can minimize the amount of moisture in contact with the wearer's skin and enhance air circulation in areas contacting the wearer's skin.

SUMMARY OF THE INVENTION

The current invention addresses the foregoing and other drawbacks and issues associated with existing disposable diapers. In accordance with one aspect of the current invention, an absorbent pant is provided with a containment system comprising a three-dimensional structure defined by a wearer-facing layer of the absorbent pant.

More particularly, the absorbent pant may include a front section terminating in a front end, a back section terminating in a back end, a seat section interconnecting the front and back sections, a length extending between the front end and the back end, a pair of opposing side edges extending along the length, a width extending between the opposing side edges, an absorbent layer of each of the front section, back section, and seat section comprising an absorbent material, and a wearer-facing layer of each of the front section, back section, and seat section superposed over the absorbent layer, the wearer-facing layer comprising a liquid permeable material. The containment system may be defined by the wearer-facing layer of at least one of the front section, the back section, and/or the seat section.

In accordance with another form, an absorbent pant is provided with a containment system defined on a wearing-facing surface of the absorbent pant. The containment system comprises at least one of the following: a pleated section comprising a plurality of pleats; a channeled section comprising a plurality of alternating ridges and channels; and a bubbled section comprising a plurality of hemispherical-shaped bubbles aligned in a plurality of rows.

In accordance with another form, a disposable absorbent pant is provided with a containment system. The absorbent pant has a front section, back section, a seat section extending between the front and back sections, and an inner, wearer-facing surface of each section. The containment system comprises a pleated section comprising a plurality of pleats disposed on at least a portion of the wearer-facing surface of at least one of the front section and the back section. In addition, the containment system comprises at least one channeled section comprising a plurality of alternating ridges and channels disposed on at least a portion of the wearer-facing surface of the seat section and/or at least one bubbled section comprising a plurality of hemispherical-shaped bubbles aligned in a plurality of rows.

BRIEF DESCRIPTION OF THE DRAWINGS

Embodiments of the present invention will now be described, by way of example only, with reference to the following drawings.

DESCRIPTION OF THE PREFERRED EMBODIMENTS

Referring to FIGS. 1-5, a disposable diaper 100 is shown in accordance with one aspect of the invention. The diaper 100 includes a front section 102, a back section 104, and a seat section 106 interconnecting the front and back sections 102 and 104, respectively. The diaper 100 has a pair of longitudinal side edges, 120 and 122, and a pair of opposite waist edges, respectively designated front waist edge 124 and back waist edge 126. The front section 102 can be contiguous with the front waist edge 124 and the back section 104 can be contiguous with the back waist edge 126.

When in use on a wearer's body, the front section 102 may be positioned at least in part in front of the wearer's body, while the back section 104 may be positioned at least in part in back of the wearer's body. The seat section 106 may be positioned between the legs of the wearer and can partially cover the seat and lower torso of the wearer. The front and back waist edges, 124 and 126 may be configured to encircle the wearer's waist in use to define a waist opening.

Figure 1:
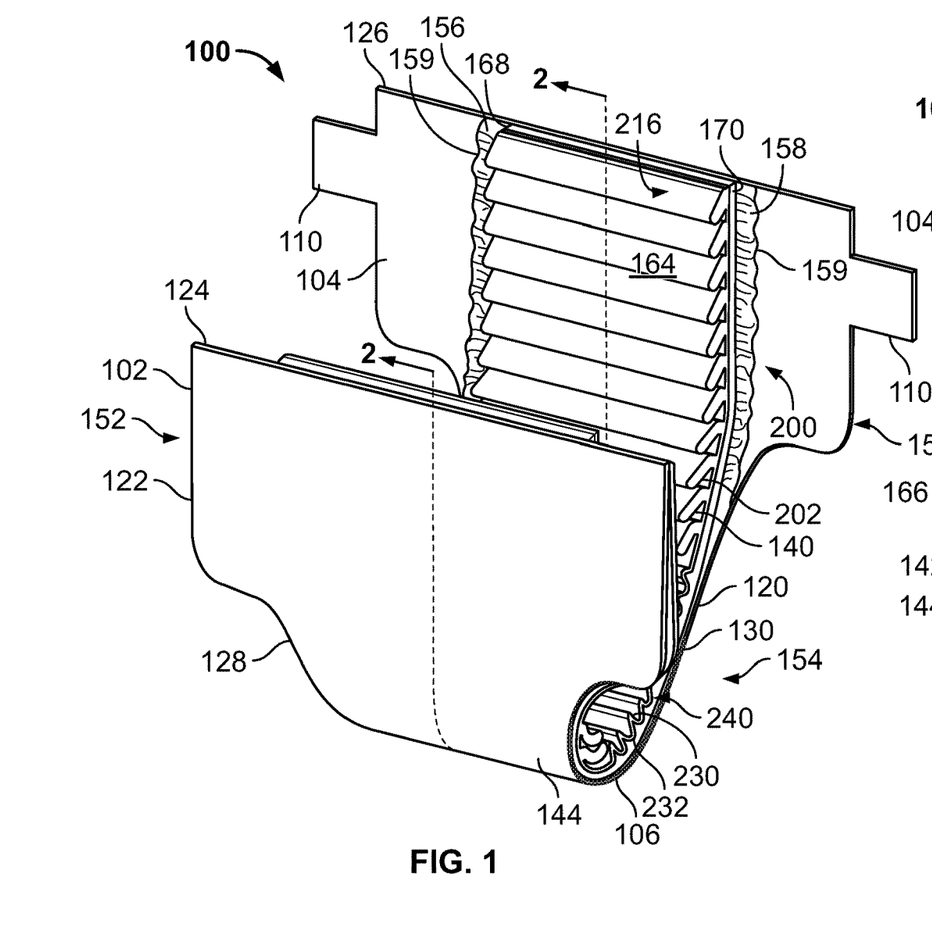
FIG. 1 is a perspective view of a disposable diaper having a containment system in accordance with one aspect of the invention.
Figure 3:
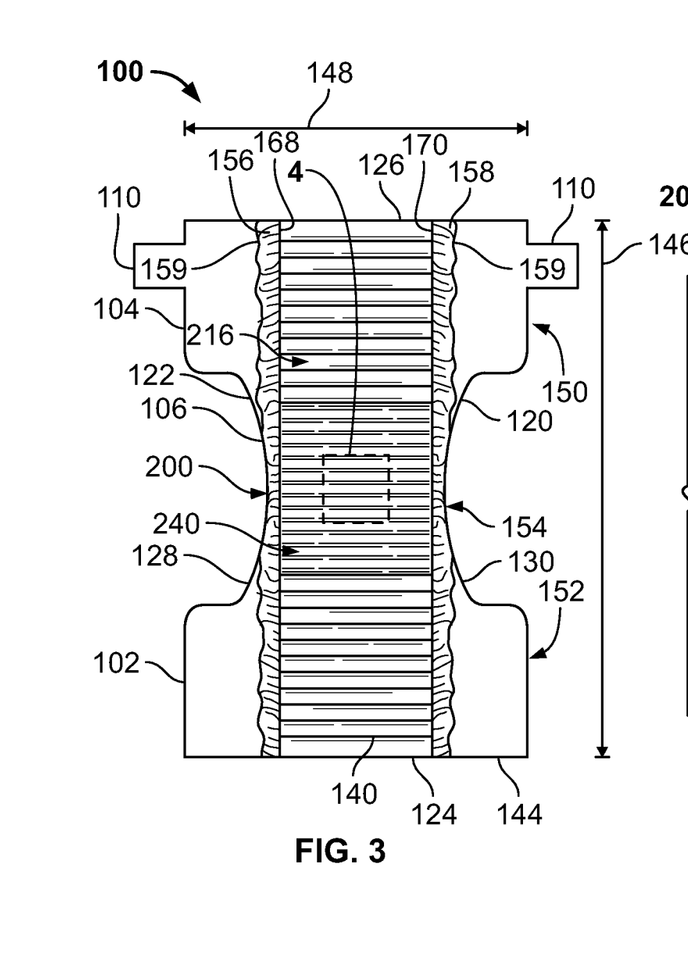
FIG. 3 is a top plan view of the diaper of FIG. 1.
Figure 4:
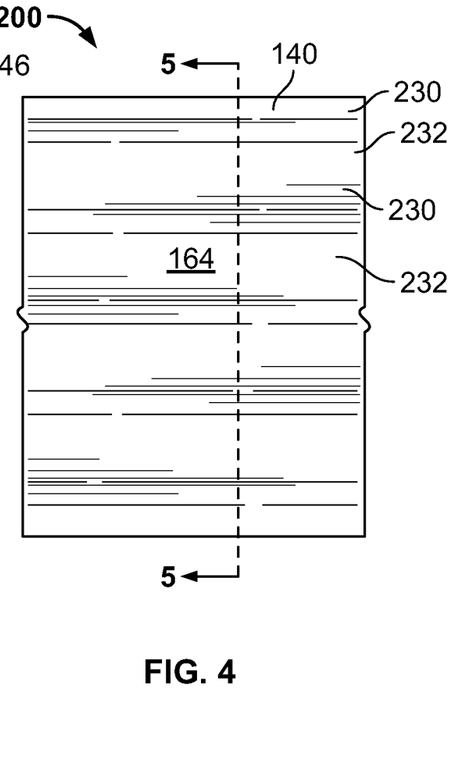
FIG. 4 is an enlarged view of the portion of the diaper marked 4 in FIG. 3.

Longitudinal side edges 120, 122 may be generally straight, or as illustrated in FIGS. 1 and 3, for example, the longitudinal side edges 120, 122 may be contoured such that the diaper 100 is wider near the front and back waist edges 124, 126 and narrower near the seat section 106. The longitudinal side edges 120, 122 generally define a pair of leg openings, 128 and 130, when the diaper 100 is in use on a wearer's body.

Figure 2:
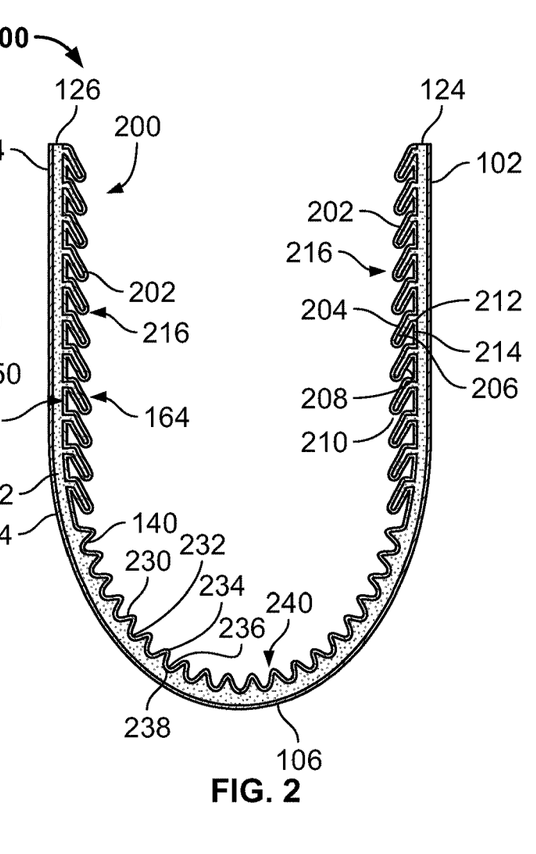
FIG. 2 is a cross-section view of the diaper of FIG. 1 taken along the line 2-2.
Figure 5:
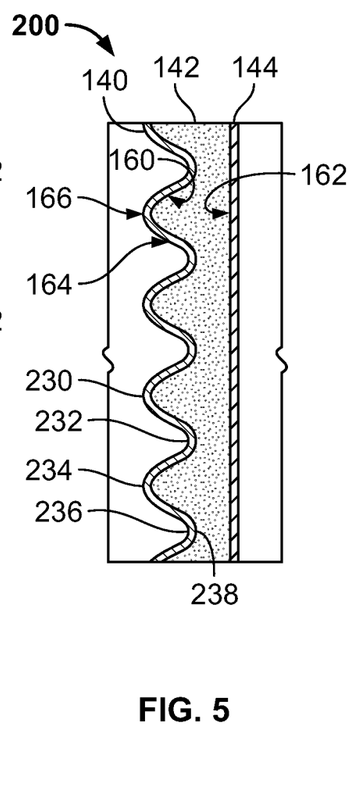
FIG. 5 is a cross-section view of the diaper taken along the line 5-5 in FIG. 4.

As shown in FIGS. 2 and 5, in accordance with one aspect of the invention, diaper 100 includes an inner or wearer-facing layer 140 that faces the wearer's body in use, an outer layer 144 that faces away from the wearer's body in use, and an absorbent layer 142 disposed between the inner layer and the outer layer. The outer layer 144 can define a length or longitudinal direction 146, and a width or lateral direction 148, which, in the illustrated embodiment, can coincide with the length and width of the diaper 100.

As shown in FIG. 3, due to the contour of longitudinal side edges 120, 122, the width 148 of the diaper 100 may vary in the longitudinal direction 146 of the diaper 100. In one form, the diaper 100 includes front and back wide portions 150 and 152, respectively, and a narrow portion 154 disposed therebetween.

The inner layer 140 and absorbent layer 142 may each have a length and width that is the same as or less than the length and width of the diaper 100. In the illustrated embodiment, the inner layer 140 and absorbent layer 142 each have a length that is approximately the same as the length of the diaper 100 and a width that is approximately the same as the width of the diaper 100 at the narrow portion 154. In another form, the width of the inner layer 140 and/or absorbent layer 142 may vary over the length of the diaper in conformity with the width 148 of the diaper.

In the illustrated embodiment, the inner layer 140 and absorbent layer 142 extend the entire length of the diaper 100 and thereby form portions of the front and back waist edges, 124 and 126, of the diaper 100.

The outer layer 144 may be formed of any suitable material and may be breathable and/or liquid impermeable. It may be elastic, stretchable, or non-stretchable. The outer layer 144 may be constructed of a single layer, multiple layers, laminates, spunbond fabrics, films, meltblown fabrics, elastic netting, microporous webs, bonded-carded webs or foams provided by elastomeric or polymeric materials.

In one form, the outer layer 144 may be a single layer of a liquid impermeable material. In an embodiment, the outer layer may be stretchable or elastic, in at least the lateral direction 148 of the diaper 100. In another form, the outer layer 144 may be stretchable or elastic in both the lateral 148 and the longitudinal 146 directions.

The outer layer 144 may be embossed and/or matte finished to provide a cloth-like appearance. The outer layer 144 may permit vapors to escape from the diaper 100 while preventing liquids from passing through. A suitable liquid impermeable, vapor permeable material can be composed of a microporous polymer film or a non-woven material which has been coated or otherwise treated to impart a desired level of liquid impermeability.

The absorbent layer 142 may be superposed over the outer layer 144. As described above, the absorbent layer 142 may have a width that is the same as or less than the width 148 of the diaper 100 and a length that is the same as or less than the length 146 of the diaper 100. In one form, the absorbent layer 142 extends longitudinally along the entire length 148 of the diaper 100 and extends laterally between the longitudinal side edges 120, 122 at the narrow portion 154 of diaper 100.

The absorbent layer 142 has at least two surfaces, a wearer-facing surface 160 and a clothing facing surface 162. In one form, the absorbent layer 142 may be bonded to the outer layer 144 by any suitable means such as, but not limited to, adhesives, ultrasonic bonds, thermal bonds, pressure bonds, or other conventional techniques. In another form, the absorbent layer 142 may simply be in contact with, and not bonded to, the outer layer 144.

The absorbent layer 142 can be suitably constructed to be generally compressible, conformable, pliable, non-irritating to the wearer's skin and capable of absorbing and retaining liquid body waste. The absorbent layer 142 may have any suitable size and/or shape and may be formed from a variety of suitable materials. The size, shape, and the absorbent capacity of the absorbent layer 142 should be compatible with the size of the intended wearer and the estimated liquid loading expected by the intended use of the diaper 100. Additionally, the size, shape, and the absorbent capacity of the absorbent layer 142 may be varied to accommodate wearers of different ages and/or different genders.

In one form, the absorbent layer 142 can be composed of a web material of hydrophilic fibers, cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In another form, the absorbent layer 142 may include superabsorbent hydrogel-forming particles and/or a matrix of cellulosic fluff and superabsorbent hydrogel-forming particles.

The absorbent layer 142 may be constructed of a single layer of materials, or in the alternative, may be constructed of two layers of materials or more. In an embodiment in which the absorbent layer 142 has two layers, the absorbent layer 142 can have a wearer-facing layer and a garment-facing layer with different absorption capacities. In one form, the wearer-facing layer may have a lower absorption capacity than the garment-facing layer. For example, the wearer-facing layer may be composed of hydrophilic fibers, and the garment-facing layer may be composed at least in part of a high absorbency material commonly known as superabsorbent material. In another form, the wearer-facing layer may be composed of cellulosic fluff, such as wood pulp fluff, and the garment-facing layer may be composed of superabsorbent hydrogel-forming particles, or a mixture of cellulosic fluff and superabsorbent hydrogel-forming particles. Alternatively, the wearer-facing layer may be composed of a mixture of hydrophilic fibers and superabsorbent material, as long as the concentration of superabsorbent material present in the wearer-facing layer is lower than the concentration of superabsorbent material present in the garment facing layer.

Various types of wettable, hydrophilic fibers can be used in the absorbent layer 142. Examples of suitable fibers include cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. For example, one suitable type of fiber is a wood pulp that is a bleached, highly absorbent sulfate wood pulp containing primarily soft wood fibers. However, the wood pulp can be exchanged with other hydrophilic fiber materials, such as synthetic, polymeric, or meltblown fibers or with a combination of meltblown and natural fibers.

Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Typically, a superabsorbent material can be capable of absorbing at least about ten times its weight in liquid. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Shapes having a largest greatest dimension/smallest dimension ratio, such as needles, flakes, and fibers are also contemplated for use herein. Conglomerates of particles of superabsorbent materials may also be used in the absorbent layer 142.

The inner layer 140 of the diaper 100 may overlay the absorbent layer 142 and the outer layer 144. The inner layer 140 may have a width that is the same as or less than the width 148 of the diaper 100 and a length that is the same as or less than the length 146 of the diaper 100. In one form, the absorbent layer 142 may extend longitudinally along the entire length of the diaper 100 and laterally between the longitudinal side edges 120, 122 at the narrow portion 154 of the diaper 100.

The inner layer 140 has at least two surfaces, a wearer-facing surface 164 and a garment-facing surface 166. A pair of longitudinal edges 168, 170 defines the width of the inner layer 140.

The inner layer 140 may be bonded to the absorbent layer 142 and/or outer layer 144. In one form, the inner layer 140 may extend laterally beyond the absorbent layer 142 to overlay a portion of the outer layer 144 and can be bonded directly thereto. For example, the inner layer 140 may be bonded to the outer layer 144 at the longitudinal edges 168, 170 on the inner layer 140. The inner layer 140 may be bonded to the outer layer 144 continuously along the entire length of the inner layer 140, or it may be bonded at discrete bonding points or bonding areas.

The inner layer 140 may be narrower than the outer layer 144 or it may have the same dimensions as outer layer 144. It is also contemplated that the inner layer 140 may not extend beyond the absorbent layer 142. In such case, the inner layer may not be bonded to the outer layer 144, but may instead be bonded to the absorbent layer 142. In yet another form, the inner layer 140, absorbent layer 142, and outer layer 144 may all be bonded together.

The inner layer 140 may be bonded to the absorbent layer 142 and/or outer layer 144 by any suitable means such as, but not limited to, adhesives, ultrasonic bonds, thermal bonds, pressure bonds, other conventional techniques, and/or combinations thereof.

The inner layer 140 may be formed of any suitable material that is sufficiently porous to be liquid permeable to thereby permit liquid to penetrate through its thickness to reach the absorbent layer 142. The inner layer 140 is preferably suitably compliant, soft feeling, and non-irritating to the wearer's skin. It may be less hydrophilic than the absorbent layer 142 to provide a relatively dry surface to the wearer and permit liquid body waste to readily penetrate through its thickness.

The inner layer 140 may be formed from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics may be used for the inner layer 140. For example, the inner layer 140 may be composed of a meltblown or spunbond web of polyolefin fibers. Alternatively, the inner layer 140 may be a bonded-carded web composed of natural and/or synthetic fibers. The inner layer 140 may be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire inner layer 140 or it can be selectively applied to particular sections of the inner layer 40.

In one form, the inner layer 140 may be stretchable or elastic, in at least the lateral direction 148 of the diaper 100. In another form, the inner layer 140 may be stretchable or elastic in both the lateral 148 and the longitudinal 146 directions.

In accordance with another aspect of the invention, the inner layer 140 and absorbent layer 142 are configured to form a containment system 200 on the wearer-facing surface 164 of the inner layer 140.

In one form, as shown, for example, in FIGS. 1 and 2, the containment system 200 may include a plurality of generally laterally-aligned pleats or shutters 202. In one form, each of pleats 202 may be in the form of a knife pleat, or a single pleat folded in one direction. Each of pleats 202 may include a portion of inner layer 140 and absorbent layer 142 folded under an adjacent portion of the inner layer 140. The portion of the inner layer 140 is folder under itself at a pleat fold 210 with a portion of the absorbent layer 142 disposed between the two layers of inner layer 140 material. Thus, as illustrated in FIG. 3, each pleat 202 may include a pleat top layer 204, which faces the wearer in use, a pleat bottom layer 208, which faces away from the wearer in use, and an absorbent core 206 therebetween.

In one form, the pleat 202 may have a substantially rigid, or fixed predetermined arrangement irrespective of the position of the diaper. That is, the pleat 202 may maintain substantially the same folded under arrangement regardless of whether the diaper is laid out flat or in use on a wearer's body. The pleat 202 may be secured in place by selectively bonding at least the pleat bottom layer 208 to the absorbent layer 142 at a pleat bonded area 212. As can be seen in FIG. 2, in one form, the pleat bonded area 212 is at or near the opposite end of the pleat from the pleat fold 210. In one form, pleat bonded area 212 may be continuous across the lateral direction of the pleat 202. However, other configurations of bonded area 212 are contemplated. Pleat bonded area 212 may be formed by any suitable means including, but not limited to, adhesives, ultrasonic bonds, thermal bonds, pressure bonds, other conventional techniques, and/or combinations thereof.

Again with reference to FIGS. 2 and 3, pleats 202 are preferably directed downward relative to the front and back waist edges 124, 126 of diaper 100. Thus, each pleat 202 thereby forms a generally downwardly opening pocket 214.

In accordance with another aspect, a plurality of generally laterally aligned pleats 202 may be disposed on at least a portion of at least one of the front section 102 and the back section 104 of the diaper 100 thereby forming at least one longitudinally-extending pleated section 216. In the illustrated form, diaper 100 includes two pleated sections 216, one extending longitudinally along at least a portion of the front section 102 and another one extending longitudinally along at least a portion of the back section 104. In accordance with one aspect, each pleated section 216 may extend longitudinally along at least one-third (⅓) of the length 146 of the diaper 100. As illustrated, pleated sections 216 may extend longitudinally up to, and thereby form portions of, the front and back waist edges, 124 and 126 of the diaper 100. In yet another form, a single pleated section 216 may extend over the entire length 146 of diaper 100.

Unlike conventional diapers, which generally have a flat inner surfaces, pleats 202, and in particular, pockets 214, advantageously provide diaper 100 a three-dimensional structure capable of physically capturing and containing excess liquid and/or waste that is not immediately absorbed by the diaper or that is too large to permeate the liquid permeable inner layer 140.

Rather than collecting on the inner surface of the diaper, and/or potentially escaping from the diaper at the front or back waist edge of the diaper, excess liquid and/or solid waste may be captured and contained in one or more pockets 214. Pleats 202 disposed at or near the front and/or back waist edges 124, 126 of diaper 100 may thereby be particularly advantageous in reducing the incidence of blowouts. In addition, since a second layer of absorbent material—the absorbent core 206—is sandwiched between the top and bottom layers 204, 208 each pleat 202 provides additional absorption capacity for excess liquid.

In accordance with yet another aspect of the invention (as illustrated in FIGS. 1-5), containment system 200 may include a plurality of generally laterally aligned ridges 230 defined by the inner layer 140. Ridges 230 may be longitudinally spaced apart from adjacent ridges 230 by generally laterally aligned depressed channels 232. As illustrated in FIGS. 2 and 5, for example, ridges 230 may have generally convexly curved peaks 234, while channels 232 may have generally concavely curved valleys 236.

The channels 232 may be formed by selectively bonding the inner layer 140 to the absorbent layer 142 at valley bonded areas 238. Valley bonded areas 238 may be formed by any suitable means including, but not limited to, adhesives, ultrasonic bonds, thermal bonds, pressure bonds, other conventional techniques, and/or combinations thereof.

In one form, a plurality of generally laterally aligned ridges 230 and channels 232 may be disposed on at least a portion of the seat section 106 of the diaper 100 thereby forming at least one longitudinal channeled section 240. In one form (as illustrated in FIGS. 1-3, for example), channeled section 240 may be positioned generally in the middle of the diaper 100 and may extend longitudinally a length of up to about one-third (⅓) of the length 146 of the diaper. Other configurations, for example, channeled sections 240 of shorter or longer lengths are also contemplated.

As with pleated sections 216, channeled sections 240 may advantageously physically capture and containing excess liquid and/or waste that is not immediately absorbed by the diaper 100 or that is too large to permeate the liquid permeable inner layer 140. Additionally, unlike traditional diapers with flat inner surfaces, channeled sections 240 provide the diaper 100 with a three-dimensional structure that may minimize the amount of moisture in contact with the wearer's skin and enhance air circulation near the wearer's skin. In particular, when the diaper 100 is positioned on the wearer's body, with the channeled section 240 disposed in the seat section 206 of the diaper, the channels 232, which are depressed relative to the adjacent ridges 230, will create spaces between the inner layer 140 and the wearer's skin. Compared to traditional diapers with flat inner surfaces, these spaces may advantageously reduce contact between wet material of the inner layer 140 and the wearer's skin and allow for increased air circulation in the area.

In accordance with still another aspect of the invention (illustrated in FIGS. 6-10), containment system 200 may include a plurality of generally hemispherical bumps or bubbles 250 on inner layer 140. In one form, bubbles 250 may be generally laterally aligned in a plurality of lateral rows 252. In addition, the bubbles 250 of one lateral row 252 may also be generally longitudinally aligned with the bubbles 250 of adjacent lateral rows 252. Each of bubbles 250 may be encircled by a generally annular depressed area 254 formed by bonding the inner layer 140 to the absorbent layer 142. Again, the depressed areas 254 may be formed by any suitable means of bonding including, but not limited to, adhesives, ultrasonic bonds, thermal bonds, pressure bonds, other conventional techniques, and/or combinations thereof.

In one form, a plurality of lateral rows 252 of bubbles 250 and depressed areas 254 may be disposed on at least a portion of the seat section 106 of the diaper 100 thereby forming at least one longitudinal bubbled section 256. So configured, the bubbled section 256 may have an appearance similar to that of bubble wrap.

Figures 6, 7:
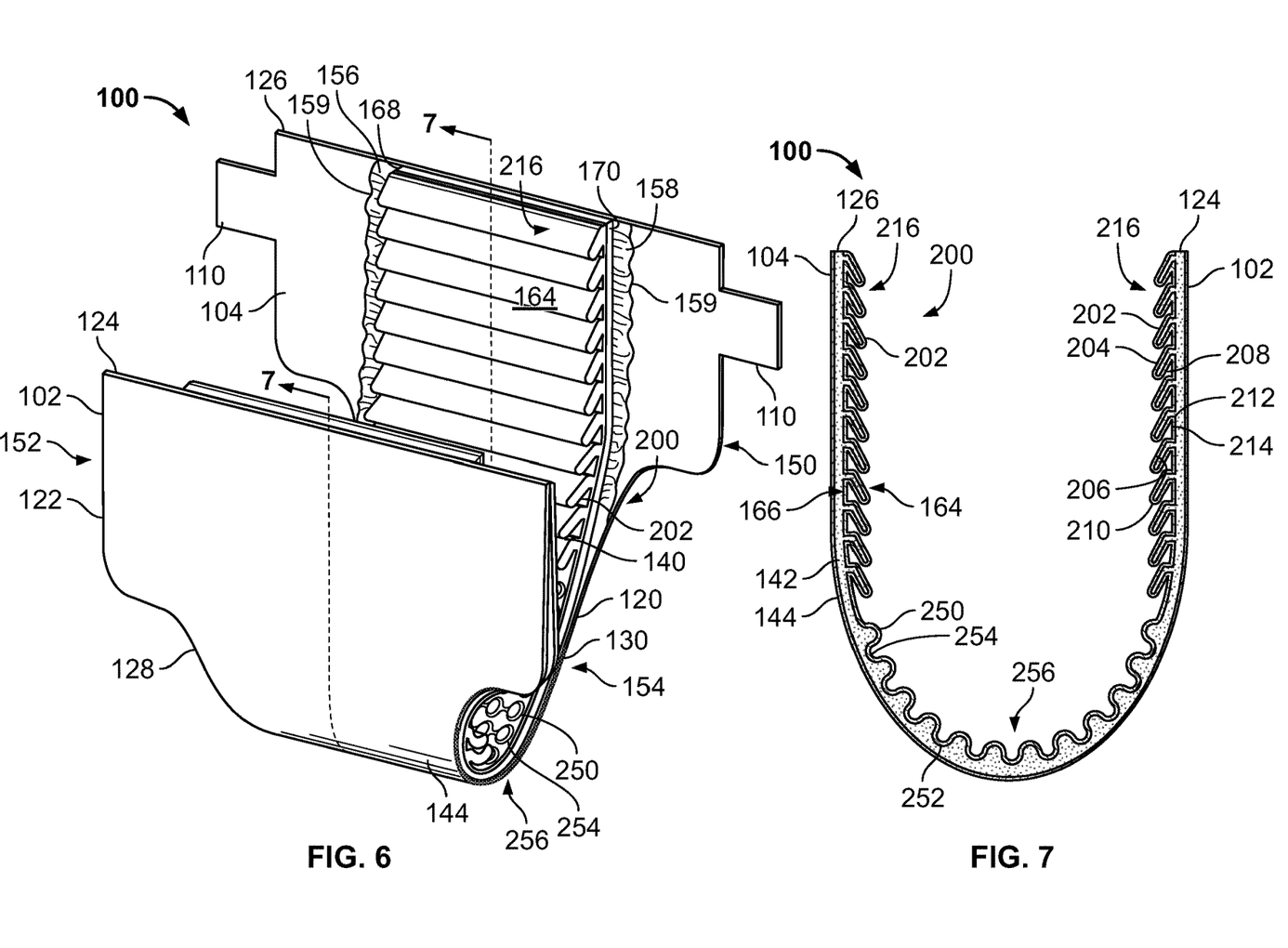
FIG. 6 is a perspective view of a diaper having a containment system in accordance with another aspect of the invention.
FIG. 7 is a cross-section view of the diaper of FIG. 6 taken along the line 7-7.
Figure 8:
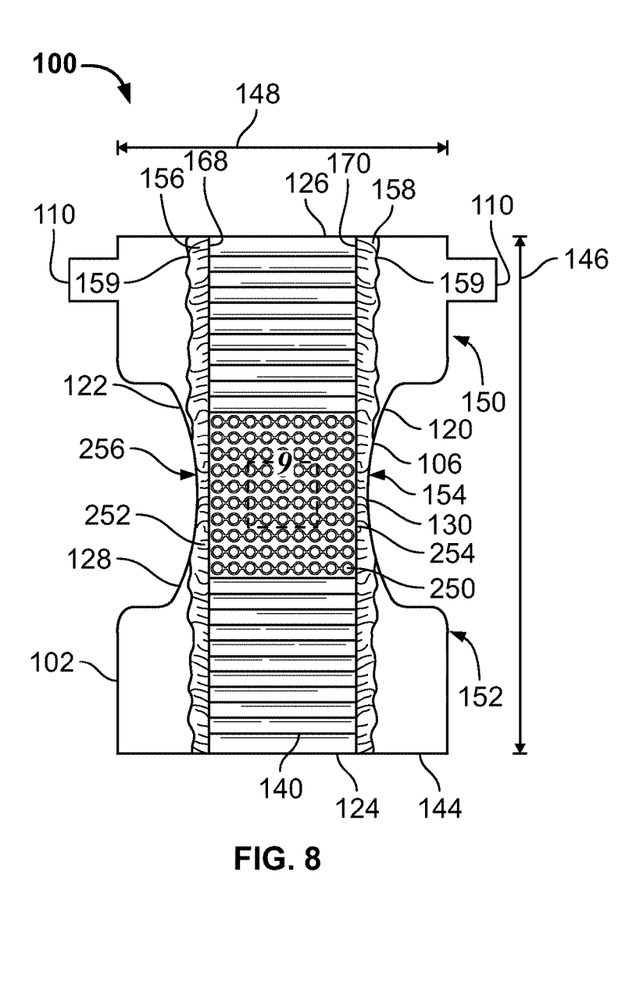
FIG. 8 is a top plan view of the diaper of FIG. 6.
Figure 9:
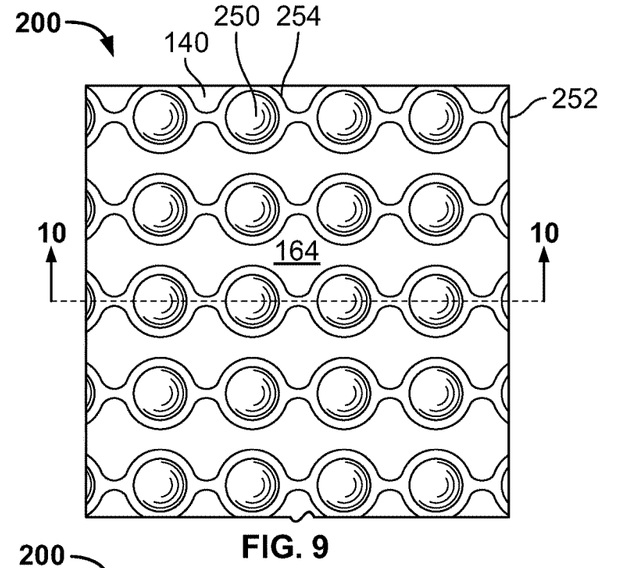
FIG. 9 is an enlarged view of the portion of the diaper marked 9 in FIG. 8.
Figure 10:
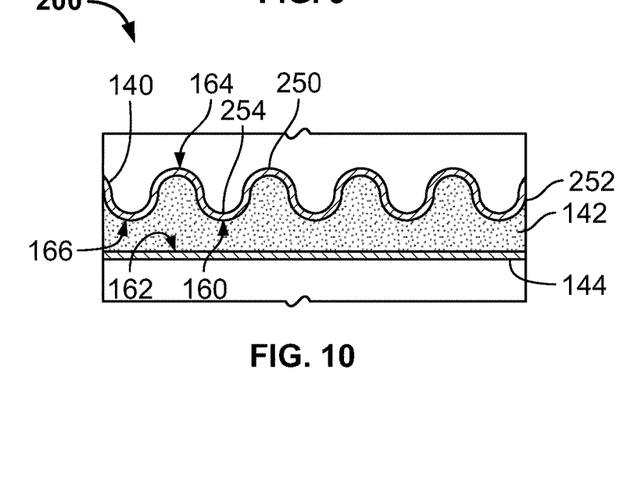
FIG. 10 is a cross-section view of the diaper taken along the line 10-10 in FIG. 9.

In accordance with another aspect (as illustrated in FIGS. 6-8, for example), bubbled section 256 may be positioned generally in the middle of the diaper 100 may extend longitudinally a length of up to about one-third (⅓) of the length 146 of the diaper. Other configurations, for example, bubble sections 256 of shorter or longer lengths are also contemplated.

As with pleated sections 216 and channeled section 240, bubbled section 256 may advantageously physically capture and contain excess liquid and/or waste that is not immediately absorbed by the diaper 100 or that is too large to permeate the liquid permeable inner layer 140. Additionally, like channeled section 240, bubbled section 256 provides the inner layer 140 of diaper 100 with a three-dimensional structure that may minimize the amount of moisture in contact with the wearer's skin and enhance air circulation near the wearer's skin. In particular, when the diaper 100 is positioned on the wearer's body, with the bubbled section 256 disposed in the seat section 106 of the diaper, the depressed areas 254, which are depressed relative to the bubbles 250, will create spaces between the inner layer 140 and the wearer's skin. These spaces may advantageously minimize contact between wet material of the inner layer 140 and the wearer's skin and allow for enhanced air circulation in the area.

As illustrated, for example, in FIGS. 1, 3, 6, and 8, diaper 100 may include various additional structures configured to contain and/or absorb liquid and solid wastes discharged from the wearer. For example, a pair of generally parallel, longitudinal flaps 156, 158 may be disposed along the longitudinal side edges, 120 and 122. The longitudinal flaps 156, 158 may extend longitudinally along the entire length 146 of diaper 100 or a part of the length 146 of the diaper 100. The longitudinal flaps 156, 158 may be configured to provide a barrier to the lateral flow of liquid and/or waste and thereby inhibit leaking at the longitudinal side edges of the diaper 120, 122. The longitudinal flaps 156, 158 may each include a free elastic edge 159, which may form an elastic cuff that closely encircles the wearer's legs in use.

Diaper 100 may also include a fastener system. The fastener system may include one or more fasteners 110. In one form, fasteners 110 may include fastener tabs 112, 114 extending laterally outwardly from at least one of the front section 102 and/or back section 104 of the diaper 100. As illustrated, the fastener tabs 112, 114 may extend outwardly from the diaper at or near at least one of the front waist edge and/or back waist edge 124, 126 of the diaper 110. The fastener tabs 110 extending from one of the front or back section 102, 104 may be secured to the other section to thereby secure the diaper 100 about the waist of the wearer and maintain the diaper in place during use. In another form, the fastener tabs 110 may include one or more materials bonded together to form a composite fastener as is known in the art. For example, the composite fastener may be composed of a stretch component, a nonwoven carrier or hook base, and a fastening component.

In another form, in which the diaper 100 may be a training pant, youth pant, diaper pant, or adult absorbent pant, and the like, the fastener system may be replaced by elastic side panels (not shown). As is known in the art, the side panels may extend between the front and back sections 102, 104 and maintaining the diaper 100 in its use position similar to traditional underwear.

In yet another form, diaper 100 may include elastic areas at or near one or both of the front waist edge 124 and/or back waist edge 126. This may permit the waist opening of the diaper 100 to closely encircle the wearer's waist in use.

Although certain presently preferred embodiments of the invention have been illustrated and described herein, it will be apparent to those skilled in the art to which the invention pertains that variations and modifications of the described embodiments may be made without departing from the spirit and scope of the invention.

What is claimed is:

1. A diaper having a front section, back section, a seat section extending between the front and back sections, and a wearer-facing layer of each section, the diaper comprising:
a three-dimensional containment system defined by the wearer-facing layer of the diaper, the containment system comprising a first pleated section defined on at least a portion of the back section of the diaper, the first pleated section comprising a plurality of pleats, with each of the pleats being aligned generally parallel to a width of the diaper and being substantially fixed in a knife pleat arrangement with a generally downwardly opening pocket facing generally toward the front section of the diaper, and a second pleated section defined on at least a portion of the front section of the diaper, the second pleated section comprising a plurality of pleats, with each of the pleats being aligned generally parallel to a width of the diaper and being substantially fixed in a knife pleat arrangement with a generally downwardly opening pocket facing generally towards the back section of the diaper.

2. The diaper of claim 1, wherein the diaper further comprises an absorbent layer and wherein each of the pleats comprises a first portion of the wearer-facing layer folded under a second portion of the wearer-facing layer with a portion of the absorbent layer positioned therebetween.

3. The diaper of claim 1, wherein the containment system further comprises a channeled section comprising a plurality of alternating ridges and channels, with each of the ridges and channels being aligned generally parallel to the width of the diaper.

4. The diaper of claim 3, wherein the channeled section is defined by the wearer-facing layer of at least a portion of the seat section of the diaper.

5. The diaper of claim 1, wherein the containment system further comprises a bubbled section comprising a plurality of hemispherical-shaped bubbles aligned in a plurality of rows, with each of the rows being aligned generally parallel to the width of the diaper.

6. The diaper of claim 5, wherein the bubbled section is defined by the wearer-facing layer of at least a portion of the seat section of the diaper.

7. A diaper comprising:
a front section terminating in a front waist edge;
a back section terminating in a back waist edge;
a seat section extending between the front and back sections,
a wearer-facing layer of each section;
a pair of fasteners extending laterally outwardly from the back section; and
a three-dimensional containment system defined by the wearer-facing layer of the diaper, the containment system comprising a first pleated section defined on at least a portion of the back section of the diaper, the first pleated section comprising a plurality of pleats, with each of the pleats being aligned generally parallel to a width of the diaper and being substantially fixed in a knife pleat arrangement with a pleat opening facing generally away from the back waist edge.

8. The diaper of claim 7, wherein the diaper further comprises an absorbent layer and wherein each of the pleats comprises a first portion of the wearer-facing layer folded under a second portion of the wearer-facing layer with a portion of the absorbent layer positioned therebetween.

9. The diaper of claim 7, wherein the diaper further comprises a second pleated section defined on at least a portion of the front section of the diaper, the second pleated section comprising a plurality of pleats, with each of the pleats being aligned generally parallel to a width of the diaper and being substantially fixed in a knife pleat arrangement with a pleat opening facing generally away from the front waist edge.

10. The diaper of claim 7, wherein the containment system further comprises a channeled section comprising a plurality of alternating ridges and channels, with each of the ridges and channels being aligned generally parallel to the width of the diaper.

11. The diaper of claim 7, wherein the containment system further comprises a bubbled section comprising a plurality of hemispherical-shaped bubbles aligned in a plurality of rows, with each of the rows being aligned generally parallel to the width of the diaper.

\* \* \* \* \*